(12) United States Patent
Lorenz

(10) Patent No.: US 8,492,484 B2
(45) Date of Patent: *Jul. 23, 2013

(54) MEDICAL DEVICES COMPRISING A CO-POLYMER OF A POLYAMIDE AND A POLYCARBONATE DIAMINE

(75) Inventor: Günter Lorenz, Tübingen (DE)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 716 days.

This patent is subject to a terminal disclaimer.

(21) Appl. No.: 12/599,275

(22) PCT Filed: May 9, 2008

(86) PCT No.: PCT/EP2008/003773
§ 371 (c)(1),
(2), (4) Date: Nov. 6, 2009

(87) PCT Pub. No.: WO2008/138568
PCT Pub. Date: Nov. 20, 2008

(65) Prior Publication Data
US 2011/0208232 A1 Aug. 25, 2011

(30) Foreign Application Priority Data
May 10, 2007 (EP) .................... 07009441

(51) Int. Cl.
| | |
|---|---|
| *C08L 69/00* | (2006.01) |
| *C08L 77/00* | (2006.01) |
| *C08G 69/44* | (2006.01) |
| *C08G 69/46* | (2006.01) |
| *A61K 9/00* | (2006.01) |

(52) U.S. Cl.
USPC .......... 525/433; 424/400; 424/422; 424/423; 525/420; 525/426; 525/432; 525/435; 604/96.01; 604/264; 623/1.1; 623/1.11; 623/1.13; 623/1.15

(58) Field of Classification Search
USPC .......... 525/420, 426, 432, 433, 435; 424/400, 424/422, 423; 604/96.1, 264; 623/1.1, 1.11, 623/1.13, 1.15
See application file for complete search history.

(56) References Cited

U.S. PATENT DOCUMENTS

| | | | |
|---|---|---|---|
| 4,120,928 | A | 10/1978 | Furukawa et al. |
| 5,030,693 | A | 7/1991 | Brown et al. |
| 5,068,284 | A | 11/1991 | Ullman et al. |
| 5,216,087 | A | 6/1993 | Kim et al. |
| 5,932,686 | A | 8/1999 | Hoff |
| 2003/0065107 | A1 | 4/2003 | Lacroix et al. |
| 2010/0217211 | A1 | 8/2010 | Lorenz |

FOREIGN PATENT DOCUMENTS

| | | |
|---|---|---|
| DE | 4301097 | 7/1994 |
| EP | 0275988 | 7/1988 |
| EP | 0302712 | 2/1989 |
| EP | 0600793 | 6/1994 |
| EP | 1783156 | 5/2007 |
| GB | 551820 | 3/1943 |
| GB | 803559 | 10/1958 |
| GB | 921667 | 3/1963 |
| GB | 1329032 | 9/1973 |
| JP | 63037125 | 2/1988 |
| JP | 2006036976 | 2/2006 |
| WO | WO 00/28807 | 5/2000 |
| WO | WO 02/074194 | 9/2002 |
| WO | WO 2004/069780 | 8/2004 |
| WO | WO 2005/076947 | 8/2005 |
| WO | WO 2006/053777 | 5/2006 |
| WO | WO 2008/080613 | 7/2008 |
| WO | WO 2008/138568 | 11/2008 |
| WO | WO 2008/138569 | 11/2008 |
| WO | WO 2008/138570 | 11/2008 |

OTHER PUBLICATIONS

U.S. Appl. No. 12/521,552, filed Jun. 26, 2009, Güenter.
U.S. Appl. No. 12/599,277, filed Nov. 6, 2009, Güenter.
International Search Report for WO2008/138570 mailed Sep. 18, 2008.
U.S. Appl. No. 12/599,277, filed Nov. 2, 2012, Notice of Allowance.
U.S. Appl. No. 12/599,277, filed Feb. 13, 2013, Issue Notification.

*Primary Examiner* — Ana Woodward
(74) *Attorney, Agent, or Firm* — Workman Nydegger; Jonathan Feuchtwang

(57) ABSTRACT

The present invention refers to medical devices comprising a modified Co-Polymer or to the modified Co-Polymer itself having high flexibility and high stress resistance, especially tensile strength or tear resistance, in addition to the good physical characteristics of a Block-Co-Polymers of a polyamide and a polycarbonate diamine.

24 Claims, No Drawings

MEDICAL DEVICES COMPRISING A CO-POLYMER OF A POLYAMIDE AND A POLYCARBONATE DIAMINE

CROSS-REFERENCE TO RELATED APPLICATIONS

This application is a U.S. Nationalization of PCT Application Number PCT/EP2008/003773 filed 9 May 2008, entitled "MEDICAL DEVICES COMPRISING A CO-POLYMER OF A POLYAMIDE AND A POLYCARBONATE DIAMINE," which claims the benefit of European Patent Application No. 07009441.2 filed 10 May 2007, entitled "CO-POLYMER OF A POLYAMIDE AND A POLYCARBONATE DIAMINE," the entireties of which are incorporated by reference in their entirety.

THE FIELD OF THE INVENTION

The present invention refers to medical devices comprising a modified co-polymer and the modified co-polymer itself having high flexibility and high stress resistance, especially tensile strength or tear resistance, in addition to the good physical characteristics of a block-co-polymer of a polyamide and a polycarbonate diamine.

BACKGROUND OF THE INVENTION

Block-co-polymers of a polyamide and a polyether have been used in the polymer industry for a long time and—due to their enormous range of possible applications—are found in many branches of industrial products. Recently in the area of medicinal devices good use has been made of these materials especially in implants. The most popular block-co-polymer of a polyamide and a polyether used in this field is PEBAX™, besides the polyamides, which include different sorts of Nylons. Even though these materials have certainly been used successfully, due to the strains put on the materials and the necessity to improve their characteristics in the light of growing experience coming from increasing numbers of treated patients, there clearly is a need for improved materials/elastomers allowing for an effective treatment of the patient preferably with an economical production process.

SUMMARY OF THE INVENTION

It is an object of the current invention to provide medical devices comprising modified elastomers or the modified elastomers themselves, preferably Co-Polymers having high flexibility and high stress resistance, especially tensile strength or tear resistance in addition to the good physical characteristics of the Co-Polymers.

The invention thus refers to a medical device or implant comprising a Co-Polymer producible by polymerizing a modified polyamide with a polycarbonate diamine, characterized in that the modified polyamide is producible by contacting/mixing one or more pre-polyamides with an $\alpha,\omega$-di-carboxylic acid or its alkyl ester or its acyl halides and raising the temperature to above 150° C.

The invention also refers to the corresponding Co-Polymer producible by polymerizing a modified polyamide with a polycarbonate diamine, characterized in that the modified polyamide is producible by contacting/mixing one or more pre-polyamides with an $\alpha,\omega$-di-carboxylic acid or its alkyl ester or its acyl halides and raising the temperature to above 150° C.

The invention further resides in a Co-Polymer or in a medical device comprising this Co-Polymer according to general formula XI, XIa, XIb or XIc

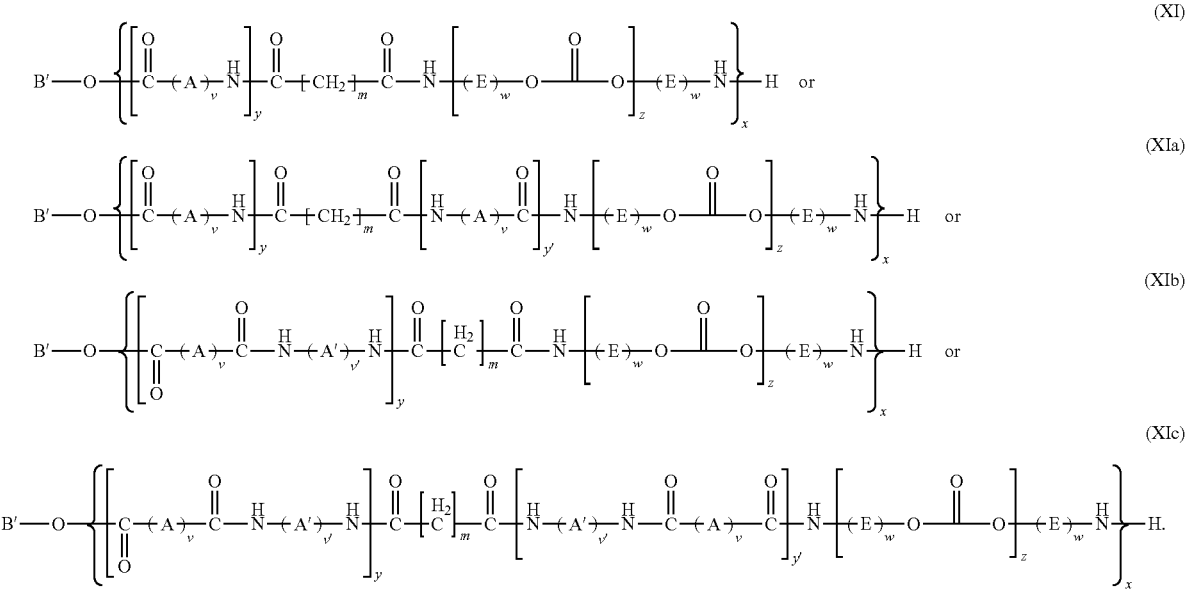

The invention furthermore resides in the use of a Co-Polymer according to the invention in the production of medical devices, balloon material, stents, stent grafts, and catheters.

DETAILED DESCRIPTION OF THE INVENTION

The use of stents, balloons, catheters and other medical devices etc. in minimal invasive surgery, especially in the cardiovascular field, has in the last years shown a high growth. As a consequence the need for useful materials fulfilling highly specialized needs in the field of different medicinal devices has clearly risen in a technical area, which traditionally is more governed by bulk products. Especially in the field of balloons used cardiovascular surgery there was a clear desire for an elastomer, which is on one hand flexible enough to be introduced into a vascular environment without causing damage, while on the other hand being stable and rigid enough, especially in the moment of actual surgery, and inflation in the vessel, to not be extended too much inside the vessel. Besides that, the material should also have a low water absorption, because its physicochemical properties, while used or while on the shelf could be severely hampered by accepting too much water, as it could also be hampered by changes during storage due to thermo-oxidation.

The invention thus refers to an implant or medical device comprising a Co-Polymer producible by polymerizing a modified polyamide with a polycarbonate diamine, characterized in that the modified polyamide is producible by contacting/mixing one or more pre-polyamides with an $\alpha,\omega$-dicarboxylic acid or its alkyl ester or its acyl halides and raising the temperature to above 150° C.

Preferably, the implant or medical device according to the invention is selected from implanted or implantable medical devices, from balloon/balloon material, stents, stent grafts, grafts, graft connectors, or catheters.

Also, the implant or medical device according to the invention may be selected from implanted or implantable medical devices or minimal invasive medical devices, from stents, stent grafts, grafts, graft connectors, closure devices, filters, or catheters, delivery catheters, stent delivery catheters, balloon dilatation catheters or medical balloons/balloon material.

In an additional embodiment, the implant or medical device according to the invention is an implanted, implantable or minimal invasive medical device, preferably is a balloon, or stent, stent graft, graft, graft connector or catheter; more preferably is a balloon catheter or a medical balloon for a medical device, most preferably is a medical balloon for a balloon catheter.

Also in one embodiment the implant or medical device according to the invention is an implanted, implantable or minimal invasive medical device, preferably is a balloon, more preferably is a balloon catheter or a medical balloon for a medical device, most preferably is a medical balloon for a balloon catheter.

"Balloon" or "balloon material" in the context of this invention especially means a balloon used in coronary balloon angioplasty and the material used for these balloons, especially balloon catheters. In this, e.g. a balloon catheter is inserted into an artery and advanced to e.g. a narrowing in a coronary artery. The balloon is then inflated to enlarge the lumen. Especially, a balloon of a balloon catheter used in minimally invasive interventions, preferably in vascular interventions, more preferably used in coronary or endovascular balloon angioplasty and the material used for these balloons. Non-invasive procedures such as percutaneous transluminal angioplasty (PTA), percutaneous transluminal coronary angioplasty (PTCA), stent delivery and deployment, radiation treatment, delivery of a drug at a lesion site and other procedures are used in the treatment of intravascular disease. These therapies are well known in the art and usually utilize a balloon catheter pulled over a guide wire. After a guiding catheter is placed into the patient's main vessel, a guide wire is advanced in the guide catheter and beyond the distal end of the guide catheter. The balloon catheter is then advanced over the guidewire until it reaches the treatment site at the lesion or stenosis. The balloon is inflated to compress the lesion site and dilate the previous narrowed lesion or stenosis site. If the balloon carried a stent and/or drug, the stent and/or drug is delivered at the site when the balloon is inflated. Likewise, further therapies may also use a balloon catheter for the treatment of the lesion site.

"Stent" means an elongate implant with a hollow interior and at least two orifices and usually a circular or elliptical, but also any other, cross section, preferably with a perforated, lattice-like structure that is implanted into vessels, in particular blood vessels, to restore and maintain the vessels patent and functional.

"Graft" means an elongate implant with a hollow interior and with at least two orifices and usually circular or elliptical, but also any other, a cross section and with at least one closed polymer surface which is homogeneous or, optionally, woven, braided, knitted or spun from various strands. The surface preferably is impermeable to corpuscular constituents of blood and/or for water, so that the implant serves as a vascular prosthesis and is usually employed for damaged vessels or in place of vessels.

"Stent graft" means a connection between a stent and a graft. A stent graft preferably comprises a vascular prosthesis reinforced with a stent (both as defined above), wherein a polymer layer is homogeneous or, optionally, woven from various strands and is impermeable for corpuscular constituents of blood and/or for water. Especially the stent graft may be woven, braided, knitted or spun from various strands and may be impermeable for corpuscular constituents of blood and/or for water or may be porous to allow endothelial ingrowth but impermeable to release of emboli or may function as a mere filter for emboli. More preferably, the stent has on at least 20% of its surface a perforated (lattice-like), preferably metallic, outer layer and at least one closed polymer layer that is located inside and/or outside the stent outer layer, or, optionally, is woven, braided, knitted or spun from various strands and may be impermeable for corpuscular constituents of blood and/or for water or may be porous to allow endothelial ingrowth but impermeable to release of emboli or may function as a mere filter for emboli. Optionally, where the closed polymer layer is disposed inside the metallic outer layer, a further perforated (lattice-like), preferably metallic, inner layer may be located inside the polymer layer.

"Graft connector" means an implant that connects at least two hollow organs, vessels or grafts, consists of the materials defined for grafts or stent grafts and/or has the structure defined for the latter. Preferably, a graft connector has at least two, three or four orifices arranged, for example, as an asymmetric "T" shape.

"Catheter" means a tubular instrument intended for introduction into hollow organs. More preferably, a catheter may be designed for use in guiding other catheters, or for angiography, ultrasound imaging, or—especially—balloon catheters for dilatation or stent delivery. This includes also a "Catheter pump" meaning a catheter provided on its tip with a propeller able to assist the pumping of the myocardium.

Most preferably, the Co-Polymer, being comprised within the implant or medical device, is used to form a medical balloon for a medical device, especially situated on or in the medical device, especially a medical balloon situated on or in a balloon catheter, which is either a balloon catheter for stent delivery or a balloon catheter for dilation, thus carrying no stent.

Accordingly, the invention also refers to a balloon for a medical device formed from a Co-Polymer according to the invention. Preferably the balloon for a medical device is formed from a length of polymer tubing by radial expansion of the tubing under pressure, the polymer being a Co-Polymer according to the invention. Even more preferably, this balloon for a medical device is formed from a length of polymer tubing by radial expansion of the tubing under pressure. The polymer being a Co-Polymer producible by polymerizing a modified polyamide with a polycarbonate diamine, characterized in that the modified polyamide is producible by contacting/mixing one or more pre-polyamides with an α,ω-di-carboxylic acid or its alkyl ester or its acyl halides and raising the temperature to above 150° C.

Especially for these embodiments it is preferable if the Co-Polymer from which the medical balloon is formed is showing certain attributes. Accordingly, for these embodiments it is preferred if the Co-Polymer according to the invention is showing one or both of the attributes listed below:
the Co-Polymer has a flexural modulus of less than about 150,000 psi; and/or
the Co-Polymer has a hardness, Shore D scale, of greater than 60.

In addition, it is also preferable for these specific embodiments for the medical balloon according to the invention to be showing one or both of the attributes listed below:
a wall strength of at least 18,000 psi, and/or
a distension over the range of 88-235 psi of at least 12%.

Also it is preferable for these specific embodiments if the medical balloon according to the invention is formed by any of the following methods with the medical balloon having proximal and distal waist portions and a central body portion:
1) radially expanding a length of polymer tubing (of the Co-Polymer according to the invention) under pressure, with said length of tubing having proximal and distal portions which are stretched to a reduced diameter and an unstretched central portion, and said radially expanding step is accomplished by expanding said tubing in a mold such that the balloon body is formed from the unstretched central portion of the tubing and the proximal and distal waist portions of the balloon are formed from the stretched proximal and distal portions of the tubing; and/or
2) extruding a tubular segment of thermoplastic material (of the Co-Polymer according to the invention) having a predetermined wall thickness and length, the segment having a proximal end, a distal end and a center portion; and drawing the segment to a predetermined length while maintaining the temperature of the segment below the highest glass transition temperature of the Co-Polymer, wherein the proximal end forms a first waist; and expanding the segment having a first waist in a mold to produce the balloon, the balloon having a body portion, wherein the center portion of said segment becomes the balloon body portion.

The invention thus refers to a Co-Polymer producible by polymerizing a modified polyamide with a polycarbonate diamine, characterized in that the modified polyamide is producible by contacting/mixing one or more pre-polyamides with an α,ω-di-carboxylic acid or its alkyl ester or its acyl halides and raising the temperature to above 150° C.

In one embodiment also one or both of the following provisos apply to the Co-Polymer according to the invention also being comprised in the implants or medical devices according to the invention:
provided that the Co-polymer is having substantially no ester linkages.
provided that the Co-polymer is having substantially no ester linkages except at the end of the Co-Polymer.

In a very preferred embodiment the α,ω-di-carboxylic acid or its alkyl ester or its acyl halides is/are not substituted.

In a preferred embodiment, the polymerization resulting in the Co-Polymer according to the invention also being comprised in the implants or medical devices according to the invention is done by contacting/mixing the modified polyamide with the polycarbonate diamine, preferably in the presence of a catalyst, preferably a Lewis base or a Lewis acid and raising the temperature to
either above 150° C. in case of a melt polymerization or above 50° C. in case of a polymerization in solution.

In a preferred embodiment—preferably drawn to the case of polymerization in solution—the raising of the temperature in the polymerization resulting in the Co-Polymer according to the invention also being comprised in the implants or medical devices according to the invention is done
a) already during the mixing/contacting and/or
b) under protective gas atmosphere, preferably under argon and/or
c) to a temperature above 200° C., preferably above 220° C. and/or
d) in 2 steps with different temperatures preferably divided by an intermediate step in which the second temperature is reached within a certain time limit and/or
e) over a time period of more than 3 h, preferably of more than 4 h.

In a preferred embodiment—preferably drawn to the case of melt polymerization—the raising of the temperature in the polymerisation resulting in the Co-Polymer according to the invention also being comprised in the implants or medical devices according to the invention is done
a) under protective gas atmosphere, preferably under argon.

In a preferable embodiment of the Co-polymer according to the invention or of the implant or medical device comprising this Co-Polymer the modified polyamide is polymerized with the polycarbonate diamine in a molar ratio of 0.9 to 1.1, preferably in equimolar amounts.

An aspect of the invention relates to the modified polyamide forming a part of the Co-Polymers according to the invention also being comprised in the implants or medical devices according to the invention, which is producible by contacting/mixing one or more pre-polyamides with an α,ω-di-carboxylic acid or its alkyl ester or its carbonyl halogen and heating to a temperature above 150° C.

In a preferred embodiment the heating for the production of the modified polyamide is done
a) already during the mixing/contacting and/or
b) under protective gas atmosphere, preferably under argon and/or
c) to a temperature above 200° C., preferably above 220° C. and/or
d) in 2 steps with different temperatures preferably divided by an intermediate step in which the second temperature is reached within a certain time limit and/or
e) over a time period of more than 3 h, preferably of more than 4 h.

Most preferably the mixing is done under protective gas atmosphere—preferably under argon—in a first heating step at more than 200° C.—preferably 220° C.—for more than 1 h—preferably 2 h. The temperature was consequently raised within 10 to 30 min—preferably within 20 min—to more than 220° C.—preferably to 250° C.—and the mixture was stirred for another 2 h.

There are 3 kinds of material used nowadays for medical devices, especially balloons, over which the material of the current invention—if compared case by case—shows advantages.
a) Nylon: Over Nylon, coming in different sorts, especially Nylon-12, the Co-Polymers of the invention show the advantage, that they are more flexible and/or have a lower water absorption. Especially the lack of flexibility is often considered as a drawback in medical devices using Nylon.

b) PEBA: Over PEBA (e.g. PEBAX®) the Co-Polymers of the invention show the advantage, that they are slightly more rigid and/or have a lower water absorption, again making them superior for the intended special use and allowing a much needed compromise balancing flexibility and rigidity. In addition, the material of the invention seems to show higher stability, especially if compared to the effects of thermo-oxidation shown by PEBA and/or also an improved dimensional stability.

c) Blend of a) and b): The need for a compromise between the higher rigidity of Nylon and higher flexibility of PEBA has already resulted in blends being used. Still, these have no defined structures or phases, giving the material of the inventions which seems to have a lower water absorption also already an inherent advantage.

In the context of this invention "contacting/mixing" is understood as placing the at least 2 substances (e.g. pre-polyamide and acid or modified polyamide and polycarbonate) in physical contact, e.g. in a common container, optionally mixing them to increase the amount of areas in contact between the substances.

In the context of this invention "polymerizing" is understood as a process of reacting monomers or building blocks together to form a network of polymer chains under suitable reaction conditions.

In the context of this invention "alkyl ester" of the at least mono-substituted α,ω-di-carboxylic acid is understood as an ester between the acid function on one end of the acid and a $C_{1-6}$-alkyl group.

In the context of this invention "acyl halide" of the α,ω-di-carboxylic acid is understood as the replacement of a hydroxyl group in the acid function by a halogen atom (—C(O)—X)— preferably a chlorine atom.

Generally "at least monsubstituted" means either "mono-substituted" or "polysubstituted".

An "aryl", "aryl radical" or group is understood as meaning ring systems with at least one aromatic ring but without heteroatoms even in only one of the rings. Examples are phenyl, naphthyl, fluoranthenyl, fluorenyl, tetralinyl or indanyl, in particular 9H-fluorenyl or anthracenyl radicals, which can be unsubstituted or monosubstituted or polysubstituted.

In the context of this invention "cycloalkyl radical" or group is understood as meaning saturated and unsaturated (but not aromatic) cyclic hydrocarbons (without a heteroatom in the ring), which can be unsubstituted or mono- or polysubstituted. Furthermore, $C_{3-4}$-cycloalkyl represents $C_3$- or $C_4$-cycloalkyl, $C_{3-5}$-cycloalkyl represents $C_3$-, $C_4$- or $C_5$-cycloalkyl, $C_{3-6}$-cycloalkyl represents $C_3$-, $C_4$-, $C_5$- or $C_6$-cycloalkyl, $C_{3-7}$-cycloalkyl represents $C_3$-, $C_4$-, $C_5$-, $C_6$- or $C_7$-cycloalkyl, $C_{3-8}$-cycloalkyl represents $C_3$-, $C_4$-, $C_5$-, $C_6$-, $C_7$- or $C_8$-cycloalkyl, $C_{4-5}$-cycloalkyl represents $C_4$- or $C_5$-cycloalkyl, $C_{4-6}$-cycloalkyl represents $C_4$-, $C_5$- or $C_6$-cycloalkyl, $C_{4-7}$-cycloalkyl represents $C_4$-, $C_5$-, $C_6$- or $C_7$-cycloalkyl, $C_{4-8}$-cycloalkyl represents $C_4$-, $C_5$-, $C_6$-$C_7$- or $C_8$-cycloalkyl $C_{5-6}$-cycloalkyl represents $C_5$- or $C_6$-cycloalkyl and $C_{5-7}$-cycloalkyl represents $C_5$-, $C_6$- or $C_7$-cycloalkyl. However, mono- or polyunsaturated, preferably monounsaturated, cycloalkyls also in particular fall under the term cycloalkyl as long as the cycloalkyl is not an aromatic system. The cycloalkyl radicals are preferably cyclopropyl, 2-methylcyclopropyl, cyclopropylmethyl, cyclobutyl, cyclopentyl, cyclopentylmethyl, cyclohexyl, cycloheptyl, cyclooctyl, and also adamanty.

A "heterocyclyl", a "heterocyclyl radical" or group or "heterocyclic ring system" is understood as meaning heterocyclic ring systems which contain one or more heteroatoms from the group consisting of nitrogen, oxygen and/or sulfur in the ring or ringsystem, and can also be mono- or polysubstituted. The ringsystem may consist either of only one saturated or unsaturated or even aromatic ring or may consist of 2, 3 or 4 saturated or unsaturated or even aromatic rings, which are condensed in that between two or more of the rings ring members are shared. Examples which may be mentioned from the group of heterocyclyls are furan, benzofuran, thiophene, benzothiophene, pyrrole, pyridine, pyrimidine, pyrazine, quinoline, isoquinoline, phthalazine, benzo-1,2,5-thiadiazole, imidazo-thiazole, benzothiazole, indole, benzotriazole, benzodioxolane, benzodioxane, carbazole and quinazoline.

In connection with aryl radical, cycloalkyl radical, or heterocyclyl radical, "substituted" is understood—unless defined otherwise—as meaning replacement of at least one hydrogen radical on the ring-system of the aryl radical, the cycloalkyl radical, or the heterocyclyl radical by OH, SH, =O, halogen (F, Cl, Br, I), CN, $NO_2$, COOH; $NR_xR_y$, with $R_x$ and $R_y$ independently being either H or a saturated or unsaturated, linear or branched, substituted or unsubstituted $C_{1-6}$-alkyl; by a saturated or unsaturated, linear or branched, substituted or unsubstituted $C_{1-6}$-alkyl; a saturated or unsaturated, linear or branched, substituted or unsubstituted —O—$C_{1-6}$-alkyl (alkoxy); a saturated or unsaturated, linear or branched, substituted or unsubstituted —S—$C_{1-6}$-alkyl; a saturated or unsaturated, linear or branched, substituted or unsubstituted —C(O)—$C_{1-6}$-alkyl; a saturated or unsaturated, linear or branched, substituted or unsubstituted —C(O)—O—$C_{1-6}$-alkyl; a substituted or unsubstituted phenyl. "Optionally at least monsubstituted" means either "not substituted" if the option is not fulfilled, "monosubstituted" or "polysubstituted", and "at least monsubstituted" means either "monosubstituted" or "polysubstituted".

Aliphatic radicals/groups, as referred to in the present invention, are optionally mono- or polysubstituted and may be branched or unbranched, saturated or unsaturated. Aliphatic radicals, as defined in the present invention, include alkyl, alkenyl and alkinyl radicals. Unsaturated aliphatic radicals, as defined in the present invention, include alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl.

In the context of this invention, alkyl radical or group is understood as meaning saturated and unsaturated, linear or branched hydrocarbons, which can be unsubstituted or mono- or polysubstituted. Thus unsaturated alkyl is understood to encompass alkenyl and alkinyl groups, like e.g. —CH=CH—$CH_3$ or —C≡C—$CH_3$, while saturated alkyl encompasses e.g. —$CH_3$ and —$CH_2$—$CH_3$. In these radicals, $C_{1-2}$-alkyl represents $C_1$- or $C_2$-alkyl, $C_{1-3}$-alkyl represents $C_1$-, $C_2$- or $C_3$-alkyl, $C_{1-4}$-alkyl represents $C_1$-, $C_2$-, $C_3$- or $C_4$-alkyl, $C_{1-5}$-alkyl represents $C_1$-, $C_2$-, $C_3$-, $C_4$-, or $C_5$-alkyl, $C_{1-6}$-alkyl represents $C_1$-, $C_2$-, $C_3$-, $C_4$-, $C_5$- or $C_6$-alkyl, $C_{1-7}$-alkyl represents $C_1$-, $C_2$-, $C_3$-, $C_4$-, $C_5$-, $C_6$- or $C_7$-alkyl, $C_{1-8}$-alkyl represents $C_1$-, $C_2$-, $C_3$-, $C_4$-, $C_5$-, $C_6$-, $C_7$- or $C_8$-alkyl, $C_{1-10}$-alkyl represents $C_1$-, $C_2$-, $C_3$-, $C_4$-, $C_5$-, $C_6$-, $C_7$-, $C_8$-, $C_9$- or $C_{10}$-alkyl and $C_{1-10}$-alkyl represents $C_1$-, $C_2$-, $C_3$-, $C_4$-, $C_5$-, $C_6$-, $C_7$-, $C_8$-, $C_9$-, $C_{10}$-, $C_{11}$-, $C_{12}$-, $C_{13}$-, $C_{14}$-, $C_{15}$-, $C_{16}$-, $C_{17}$- or $C_{1-8}$-alkyl. The alkyl radicals are preferably methyl, ethyl, vinyl (ethenyl), propyl, allyl (2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, if substituted also $CHF_2$, $CF_3$ or $CH_2OH$ etc.

In connection with alkylene, alkyl or aliphatic radical or group—unless defined otherwise—the term "substituted" in the context of this invention is understood as meaning replacement of at least one hydrogen radical by F, Cl, Br, I, $NH_2$, SH or OH; within that "monosubstituted" means the substitution of exactly one hydrogen radical, whereas "polysubstituted" means the substitution of more than one hydrogen radical with "polysubstituted" radicals being understood as meaning that the replacement takes effect both on different and on the same atoms several times with the same or different substituents, for example three times on the same C atom, as in the case of $CF_3$, or at different places, as in the case of e.g. —CH(OH)—CH═CH—$CHCl_2$. Therefore, "optionally at least monsubstituted" means either "not substituted" if the option is not fulfilled, "monosubstituted" or "polysubstituted", and "at least monsubstituted" means either "monosubstituted" or "polysubstituted". This definition of "substituted" or the selected substituents generally also applies to the "at least mono-substituted α,ω-di-carboxylic acid or its alkyl ester or its acyl halides" or an acid of formula I.

The term "alkylene" is understood as meaning a divalent alkyl group like —$CH_2$— or —$CH_2$—$CH_2$—, with $(CH_2)_{3-6}$ being understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, $(CH_2)_{14}$ is to be understood as meaning —$CH_2$—, —$CH_2$—$CH_2$—, —$CH_2$—$CH_2$—$CH_2$— and —$CH_2$—$CH_2$—$CH_2$—$CH_2$—, $(CH_2)_{4-5}$ is to be understood as meaning —$CH_2$—$CH_2$—$CH_2$—$CH_2$— and —$CH_2$—$CH_2$—$CH_2$—$CH_2$—$CH_2$—, etc.

In a preferred embodiment of the modified polyamide forming a part of the Co-Polymer according to the invention which may also be comprised within the implants or medical devices according to the invention the α,ω-di-carboxylic acid is selected from oxalic acid (2), malonic acid (3), succinic acid (4), fumaric acid (4), glutaric acid (5), adipic acid, 1,7-heptane-dicarboxylic acid, 1,8-octane-di-carboxylic acid, 1,9-nonane-di-carboxylic acid, 1,10-decane-di-carboxylic acid, 1,11-undecane-di-carboxylic acid, 1,12-dodecane-di-carboxylic acid; preferably from adipic acid or 1,10-decane-di-carboxylic acid.

In the context of this invention "forming a part of the Co-Polymer according to the invention" is defined as the compound "forming a part" being the source of a building block or building blocks derived from this compound during the production of the Co-Polymer according to the invention. Thus, these building blocks are being part of the Co-polymer after the final production step (e.g. the polymerisation).

In another preferred embodiment of the modified polyamide forming a part of the Co-Polymer according to the invention which may also be comprised within the implants or medical devices according to the invention the α,ω-di-carboxylic acid is a compound of general formula I $$HOOC-(CH_2)_m-COR^2 \qquad (I)$$

wherein
m is selected from a natural number between 1 and 10;
$R^2$ is selected from OH, halogen or $OC_{1-4}$-alkyl.

In another preferred embodiment of the modified polyamide according to formula I forming a part of the Co-Polymer according to the invention which may also be comprised within the implants or medical devices according to the invention
either
m is 2, 3, 4 or 5; preferably is 4;
or
m is 5, 6, 7, 8 or 9; preferably is 8;
preferably wherein
m is 2, 3, 4 or 5; preferably is 4.

In another preferred embodiment of the modified polyamide forming a part of the Co-Polymer according to the invention which may also be comprised within the implants or medical devices according to the invention the α,ω-di-carboxylic acid is adipic acid.

In another preferred embodiment of the modified polyamide forming a part of the Co-Polymer according to the invention which may also be comprised within the implants or medical devices according to the invention the pre-polyamide is a structure of general formula III or IIIa

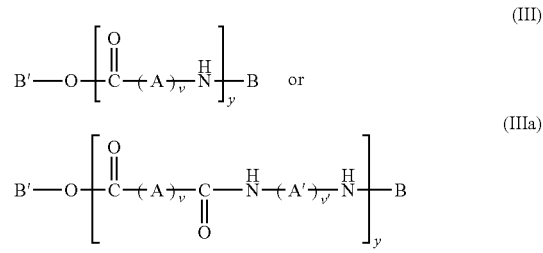

preferably a structure of general formula III, wherein
A is a divalent, branched or linear, saturated or non-saturated, optionally substituted hydrocarbon chain, with optionally at least one carbon atom being replaced by NH, O or S; preferably is a divalent, branched or linear, saturated or non-saturated, optionally substituted hydrocarbon chain, with optionally one carbon atom being replaced by NH, O or S;
A' is a divalent, branched or linear, saturated or non-saturated, optionally substituted hydrocarbon chain, with optionally at least one carbon atom being replaced by NH, O or S; preferably is a divalent, branched or linear, saturated or non-saturated, optionally substituted hydrocarbon chain, with optionally one carbon atom being replaced by NH, O or S;
B and B' independently from one another are selected from H or $C_{1-4}$-Alkyl;
v is a natural number between 1 and 24;
v' is a natural number between 1 and 24;
y is a natural number $\geq 1$.

In another preferred embodiment of the modified polyamide forming a part of the Co-Polymer according to the invention which may also be comprised within the implants or medical devices according to the invention in the pre-polyamide according to general formula III or IIIa
A is a branched or linear, saturated or non-saturated, optionally substituted divalent aliphatic group; preferably is optionally substituted alkylene; more preferably is —$CH_2$—;
A' is a branched or linear, saturated or non-saturated, optionally substituted divalent aliphatic group; preferably is optionally substituted alkylene; more preferably is —$CH_2$—;
and/or
v is a natural number between 3 and 13, preferably is a natural number between 5 and 11; more preferably is 5, 10 or 11, most preferably is 11 or 5;
v' is a natural number between 3 and 13, preferably is a natural number between 5 and 11; more preferably is 5, 10 or 11, most preferably is 11 or 5;

preferably, if the pre-polyamide is a structure according to general formula III,
A is a branched or linear, saturated or non-saturated, optionally substituted divalent aliphatic group; preferably is optionally substituted alkylene; more preferably is —$CH_2$—;
and/or
v is a natural number between 3 and 13, preferably is a natural number between 5 and 11; more preferably is 5, 10 or 11, most preferably is 11.

In another preferred embodiment of the modified polyamide forming a part of the Co-Polymer according to the invention which may also be comprised within the implants or medical devices according to the invention the pre-polyamide is selected from Nylon 6; Nylon 6,6; Nylon 11; or Nylon 12; preferably is Nylon 12.

In another preferred embodiment of the modified polyamide forming a part of the Co-Polymer according to the invention which may also be comprised within the implants or medical devices according to the invention the pre-polyamide is selected from Nylon 6; Nylon 6,6; Nylon 11; or Nylon 12; preferably is Nylon 12 and the at least mono-substituted α,ω-di-carboxylic acid is 3-tert. butyl adipic acid.

In another preferred embodiment of the modified polyamide forming a part of the Co-Polymer according to the invention which may also be comprised within the implants or medical devices according to the invention the α,ω-di-carboxylic acid is added—when producing the modified polyamide—in an amount resulting in a molar ratio between the acid and the pre-polyamide (wherein the molarity of the pre-polyamide is calculated relatively based on the equivalent number of theoretical lactam units in the pre-polyamide) of
  i. between 0.05 and 0.0005, preferably between 0.025 and 0.001; or
  ii. between 1.0 and 0.0005, preferably between 0.75 and 0.00075, and more preferably between 0.5 and 0.001, or between 0.05 and 0.004, or between 0.1 and 0.001.

In another preferred embodiment of the modified polyamide forming a part of the Co-Polymer according to the invention which may also be comprised within the implants or medical devices according to the invention the α,ω-di-carboxylic acid is added—when producing the modified polyamide—in an amount resulting in a molar ratio between the acid and the pre-polyamide calculated (wherein the molarity of the pre-polyamide is calculated relatively based on the number and molecular weight of polymerized amide building blocks (VIII))

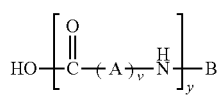 (VIII)

and the molar ratio results in
between 0.05 and 0.0005, preferably between 0.025 and 0.001; or
ii. between 1.0 and 0.0005, preferably between 0.75 and 0.00075, and more preferably between 0.5 and 0.001, or between 0.05 and 0.004, or between 0.1 and 0.001.

Thus, e.g. if mixing Y grams of di-carboxylic acid and X grams of pre-polyamide, the amount of acid is divided by its molecular weight to give the molarity, while the amount of pre-polyamide is divided by the molecular weight of the building block/the theoretical basic lactam unit to give its relative molarity. Then the relative molecular ratio of acid: pre-polyamide is calculated.

In another preferred embodiment of the modified polyamide forming a part of the Co-Polymer according to the invention which may also be comprised within the implants or medical devices according to the invention the reaction leading to the modified polyamide is executed using reactive extrusion as described in DD 276 290 A1 and Eichhorn et al. (Journal of Applied Polymer Science, Vol. 62, 2053-2060 (1996).

In another preferred embodiment of the modified polyamide forming a part of the Co-Polymer according to the invention which may also be comprised within the implants or medical devices according to the invention the modified polyamide is of general formula IV or Iva, preferably IV, wherein

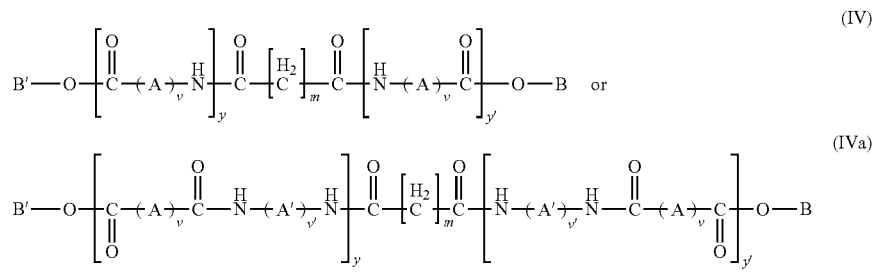

A is a divalent, branched or linear, saturated or non-saturated, optionally substituted hydrocarbon chain, with optionally at least one carbon atom being replaced by NH, O or S; preferably is a divalent, branched or linear, saturated or non-saturated, optionally substituted hydrocarbon chain, with optionally one carbon atom being replaced by NH, O or S;

A' is a divalent, branched or linear, saturated or non-saturated, optionally substituted hydrocarbon chain, with optionally at least one carbon atom being replaced by NH, O or S; preferably is a divalent, branched or linear, saturated or non-saturated, optionally substituted hydrocarbon chain, with optionally one carbon atom being replaced by NH, O or S;

B and B' independently from one another are selected from H or $C_{1-4}$-Alkyl;
v is a natural number between 1 and 24;
v' is a natural number between 1 and 24;
y is a natural number $\geq 1$;
y' is a natural number $\geq 1$ or 0;
m is a natural number between 1 and 10.

In another preferred embodiment of the modified polyamide forming a part of the Co-Polymer according to the invention which may also be comprised within the implants or medical devices according to the invention the modified polyamide is of general formula V, wherein (V)

$$B'-O+\left[\overset{O}{\underset{\|}{C}}+\left(\overset{H_2}{\underset{}{C}}\right)_v\overset{H}{\underset{}{N}}\right]_y\overset{O}{\underset{\|}{C}}\diagdown\diagdown\diagdown\overset{O}{\underset{\|}{C}}+\overset{H}{\underset{}{N}}+\left(\overset{H_2}{\underset{}{C}}\right)_v\overset{O}{\underset{\|}{C}}\right]_{y'}O-B$$

B and B' independently from one another are selected from H or $C_{1-4}$-Alkyl;
v is a natural number between 1 and 24;
y is a natural number $\geq 1$.
y' is a natural number $\geq 1$ or 0.

In another preferred embodiment of the modified polyamide forming a part of the Co-Polymer according to the invention which may also be comprised within the implants or medical devices according to the invention the modified polyamide is of general formula IV or V, wherein
B and B' are hydrogen;
and/or
v is a natural number between 3 and 13, preferably is a natural number between 5 and 11; preferably is 5, 10 or 11, more preferably is 5 or 11, most preferably is 11;
and/or
y' is 0;
and/or
y+y' is a natural number between 20 and 2000, preferably 40 and 1000.

In another preferred embodiment of the polycarbonate diamine forming a part of the Co-Polymer according to the invention which may also be comprised within the implants or medical devices according to the invention the polycarbonate diamine is of general formula VII or VIIa, wherein (VII)

$$H_2N+E\rightarrow_w\left[-O\overset{O}{\underset{\|}{\text{—}}}O+E\rightarrow_w\right]_z NH_2$$

(VIIa)

$$H_2N+\left(\overset{H_2}{\underset{}{C}}\right)_w\left[-O\overset{O}{\underset{\|}{\text{—}}}O+\left(\overset{H_2}{\underset{}{C}}\right)_w\right]_z NH_2$$

E is a divalent, branched or linear, saturated or non-saturated, optionally substituted hydrocarbon chain;
w is a natural number between 1 and 24;
z is a natural number $\geq 1$.

In another preferred embodiment of the polycarbonate diamine forming a part of the Co-Polymer according to the invention which may also be comprised within the implants or medical devices according to the invention the polycarbonate diamine is of general formula VIIa, wherein
w is a natural number between 1 and 10; preferably if z=1, w is a natural number between 1 and 10 and if z≠1, w is a natural number between 2 and 10;
and/or
z is a natural number between 1 and 2000, preferably between 2 and 2000, more preferably between 1 and 1000.

In another preferred embodiment of the Co-polymer according to the invention which may also be comprised within the implants or medical devices according to the invention
either the reaction leading to the modified polyamide; or
the polymerization reaction; or
both reactions
is/are executed using reactive extrusion as described in DD 276 290 A1 and Eichhorn et al. (Journal of Applied Polymer Science, Vol. 62, 2053-2060 (1996).

Another aspect the invention relates to Co-Polymers (B) according to general formula XI, XIa, XIb or XIc which may also be comprised within the implants or medical devices according to the invention, wherein (XI)

$$B'-O+\left\{\left[\overset{O}{\underset{\|}{C}}+A\rightarrow_v\overset{H}{\underset{}{N}}\right]_y\overset{O}{\underset{\|}{C}}+CH_2\rightarrow_m\overset{O}{\underset{\|}{C}}-\overset{H}{\underset{}{N}}+E\rightarrow_w O\overset{O}{\underset{\|}{\text{—}}}O+E\rightarrow_w\overset{H}{\underset{}{N}}\right\}_x H, \text{ or}$$

(XIa)

$$B'-O+\left\{\left[\overset{O}{\underset{\|}{C}}+A\rightarrow_v\overset{H}{\underset{}{N}}\right]_y\overset{O}{\underset{\|}{C}}+CH_2\rightarrow_m\overset{O}{\underset{\|}{C}}-\overset{H}{\underset{}{N}}+A\rightarrow_v\overset{O}{\underset{\|}{C}}\right]_{y'}\overset{H}{\underset{}{N}}+E\rightarrow_w O\overset{O}{\underset{\|}{\text{—}}}O+E\rightarrow_w\overset{H}{\underset{}{N}}\right\}_x H \text{ or}$$

(XIb)

$$B'-O+\left\{\left[\overset{}{\underset{}{C}}+A\rightarrow_v\overset{O}{\underset{\|}{C}}-\overset{H}{\underset{}{N}}+A'\rightarrow_{v'}\overset{H}{\underset{}{N}}\right]_y\overset{O}{\underset{\|}{C}}+\overset{H_2}{\underset{}{C}}\rightarrow_m\overset{O}{\underset{\|}{C}}-\overset{H}{\underset{}{N}}+E\rightarrow_w O\overset{O}{\underset{\|}{\text{—}}}O+E\rightarrow_w\overset{H}{\underset{}{N}}\right\}_x H \text{ or}$$

(XIc)

$$B'-O+\left\{\left[\overset{}{\underset{\overset{\|}{O}}{C}}+A\rightarrow_v\overset{O}{\underset{\|}{C}}-\overset{H}{\underset{}{N}}+A'\rightarrow_{v'}\overset{H}{\underset{}{N}}\right]_y\overset{O}{\underset{\|}{C}}+\overset{H_2}{\underset{}{C}}\rightarrow_m\overset{O}{\underset{\|}{C}}-\overset{H}{\underset{}{N}}+A'\rightarrow_{v'}\overset{H}{\underset{}{N}}-\overset{O}{\underset{\|}{C}}+A\rightarrow_v\overset{O}{\underset{\|}{C}}\right]_{y'}\overset{H}{\underset{}{N}}+E\rightarrow_w O\overset{O}{\underset{\|}{\text{—}}}O+E\rightarrow_w\overset{H}{\underset{}{N}}\right\}_x H.$$

A is a divalent, branched or linear, saturated or non-saturated, optionally substituted hydrocarbon chain, with optionally one carbon atom being replaced by NH, O or S;

A' is a divalent, branched or linear, saturated or non-saturated, optionally substituted hydrocarbon chain, with optionally one carbon atom being replaced by NH, O or S;

E is a divalent, branched or linear, saturated or non-saturated, optionally substituted hydrocarbon chain;

B' is selected from H or $C_{1-4}$-Alkyl;

v is a natural number between 1 and 24;

v' is a natural number between 1 and 24;

w is a natural number between 1 and 24;

x is a natural number $\geq 1$;

y and y' are independently from one another a natural number $\geq 1$;

z is a natural number $\geq 1$;

m is a natural number between 1 and 10.

In another preferred embodiment of the Co-Polymer (B) according to the invention the Co-Polymer is of general formula XIII or XIIIa which may also be comprised within the implants or medical devices according to the invention, wherein and y' is a natural number between 1 and 2000, preferably 2 and 1000, more preferably between 2 and 200, even more preferably between 2 and 150, most preferably between 2 and 100;

and the sum of y+y' is a natural number between 1 and 2000, preferably between 2 and 1000, more preferably between 2 and 200, even more preferably between 2 and 150, most preferably between 2 and 100;

and/or x is a natural number between 1 and 100.

In another preferred embodiment of the Co-Polymer (B) according to the invention according to general formula XII or XIII which may also be comprised within the implants or medical devices according to the invention in the Co-Polymer (B)

v is 11; and w is 6.

In another preferred embodiment of the Co-Polymer according to the invention which may also be comprised within the implants or medical devices according to the invention the Co-Polymer is modified in at least one of the end groups with liquid crystalline oligomers (LCOS/LC-oligomers).

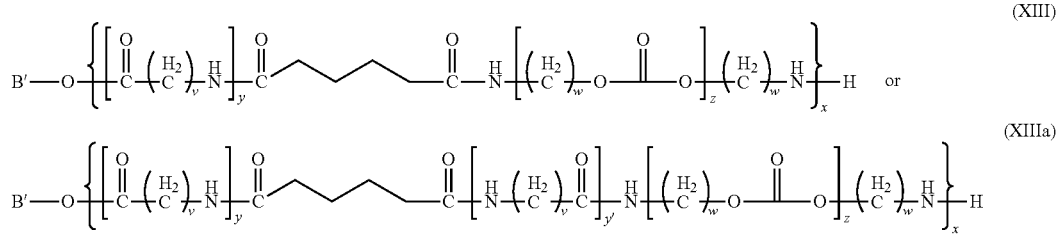

B' is selected from H or $C_{1-4}$-Alkyl;

v is a natural number between 1 and 24;

w is a natural number between 1 and 24;

x is a natural number $\geq 1$;

y and y' are independently from one another a natural number $\geq 1$:

z is a natural number $\geq 1$.

In another preferred embodiment of the Co-Polymer (B) according to the invention according to general formula XI, XIa, XIb, XIc, or XIII, XIIIa which may also be comprised within the implants or medical devices according to the invention in the Co-Polymer B' is hydrogen;

and/or

A is —$CH_2$—;

and/or

E is —$CH_2$—;

and/or v is a natural number between 3 and 13, preferably is a natural number between 5 and 11; preferably is 5, 10 or 11, more preferably is 5 or 11, most preferably is 11;

and/or w is a natural number between 1 and 10; preferably if z=1, w is a natural number between 1 and 10 and if z≠1, w is a natural number between 2 and 10;

and/or z is a natural number between 1 and 2000, preferably between 2 and 2000, more preferably between 1 and 1000;

and/or y is a natural number between 1 and 2000, preferably 2 and 1000, more preferably between 2 and 200, even more preferably between 2 and 150, most preferably between 2 and 100;

Another aspect of the invention provides a Co-Polymer (C) which may also be comprised within the implants or medical devices according to the invention comprising units derived from polyamide-forming monomers, units derived from polycarbonate diamines and units derived from α,ω-di-carboxylic acids, wherein the polyamide-forming monomers are represented by the following formulas (IX) or (IXa), the polycarbonate diamines are represented by the following formula (VII) or (VIIa) and the α,ω-di-carboxylic acids are represented by the following formula (I):

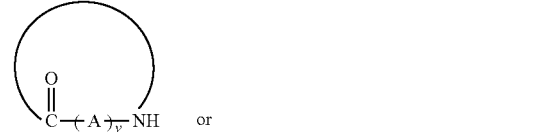

wherein

A is a divalent, branched or linear, saturated or non-saturated, optionally substituted hydrocarbon chain, with optionally one carbon atom being replaced by NH, O or S; preferably is methylene, and v is a natural number between 1 and 24; preferably is a natural number between 3 and 13, more preferably is a natural number between 5 and 11; more preferably is 5, 10 or 11, even more preferably is 5 or 11, most preferably is 11;

with

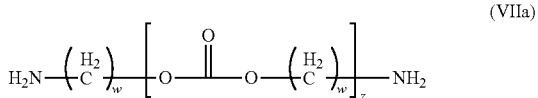

wherein

E is a divalent, branched or linear, saturated or non-saturated, optionally substituted hydrocarbon chain; preferably is methylene;

w is a natural number between 1 and 24;

z is a natural number $\geq 1$;

with

wherein m is selected from a natural number between 1 and 10; preferably m is 2, 3, 4 or 5, more preferably is 4;

$R^2$ is selected from OH, halogen or $OC_{1-4}$-alkyl, preferably is OH.

In a preferred embodiment of the Co-Polymer (C) according to the invention outlined above which may also be comprised within the implants or medical devices according to the invention A is —CH—;

and/or v is a natural number between 3 and 13, preferably is a natural number between 5 and 11; preferably is 5, 10 or 11, more preferably is 5 or 11, most preferably is 11;

and/or

E is —CH—;

and/or w is a natural number between 1 and 10; preferably if z=1, w is a natural number between 1 and 10 and if z≠1, w is a natural number between 2 and 10;

and/or z is a natural number between 1 and 2000, preferably between 2 and 2000, more preferably between 1 and 1000;

and/or m is selected from a natural number between 1 and 10;

and/or $R^2$ is selected from OH, halogen or $OC_{1-4}$-alkyl.

In a preferred embodiment of the Co-Polymer (C) according to the invention outlined above which may also be comprised within the implants or medical devices according to the invention the Co-Polymer contains the units derived from polyamide-forming monomers in an amount of 15 to 90 weight %.

In another preferred embodiment of the Co-Polymer (C) according to the invention outlined above which may also be comprised within the implants or medical devices according to the invention the Co-Polymer contains the units derived from polycarbonate diamines in an amount of 15 to 90 weight %.

Another aspect of the invention provides a process for the production of a modified polyamide forming a part of the Co-Polymer according to the invention, wherein one or more pre-polyamide/s is contacted/mixed with an α, ω-di-carboxylic acid, preferably adipic acid, and then the mixture is heated to a temperature above 150° C.

In another preferred embodiment of the process for the production of a modified polyamide forming a part of the Co-Polymer according to the invention the α,ω-di-carboxylic acid, preferably the adipic acid is added in an amount resulting in a molar ratio between the acid and the pre-polyamide calculated relatively based on the equivalent number of lactam Units in the pre-polyamide between 0.05 and 0.0005, preferably between 0.025 and 0.001; or between 1.0 and 0.0005, preferably between 0.75 and 0.00075, and more preferably between 0.5 and 0.001, or between 0.05 and 0.004, or between 0.1 and 0.001;

or in an amount resulting in a molar ratio between the acid and the pre-polyamide calculated relatively based on molecular weight of the polymerized amide building block (VIII)

between 0.05 and 0.0005, preferably between 0.025 and 0.001; or between 1.0 and 0.0005, preferably between 0.75 and 0.00075, and more preferably between 0.5 and 0.001, or between 0.05 and 0.004, or between 0.1 and 0.001.

In another preferred embodiment of the process for the production of a modified polyamide forming a part of the Co-Polymer according to the invention the reaction is executed using reactive extrusion.

Another aspect of the current invention provides the use of a Co-Polymer according to the invention in the production of implants or medical devices, preferably implanted or implantable medical devices, more preferably for the production of balloon/balloon material, of stents, stent grafts, grafts, graft connectors or catheters.

As described above a main aspect of the current invention provides implants or medical devices, comprising a Co-Polymer according to the invention, preferably implanted or implantable medical devices, more preferably balloon/balloon material, stents, stent grafts, grafts, graft connectors or catheters.

The examples and figures in the following section describing the use of the polyamides are merely illustrative and the invention cannot be considered in any way as being restricted to these applications.

EXAMPLES

A) The following examples A1 to A2 are examples of the production of the modified polyamide forming part of the Co-Polymer according to the invention:

Example A1

1.4%; Normal Reaction 50 g dried Nylon 12 (with a molecular weight of approx. 26000 g/mol) was mixed with 0.639 g (0.0034 mol) adipic acid under argon for 2 h at 220° C. The temperature was raised within 20 min to 250° C. and the mixture was stirred for another 2 h. The resulting solid gave a molecular weight of 13000 g/mol. The relative molar ratio (see above) was 0.013, being calculated as 0.0034 mol (acid): 0.253 rel. mol (Polyamid: MW (building block) 197.3).

Example A2

1.4%; Extrusion

The reaction of example A1 is carried out in an extruder by way of the so-called (reactive extrusion) as described in DD 276 290 A1 and Eichhorn et al. (Journal of Applied Polymer Science, Vol. 62, 2053-2060 (1996). Reaction time in each of the 2 steps is reduced to below 30 min.

C) The following example C1 is an example of the production of a Co-Polymer according to the invention:

Example C1

Co-Polymer with Polycarbonate Diamine

Modified polyamide according to example A1 is mixed with polyhexamethylene-carbonate diamine at 200° C. and the mixture is stirred for 4 h.

In some examples the modified polyamide according to example A1 is mixed with polyhexamethylene carbonate diamine in a roughly or exactly equimolar amount.

Specific amino-modified polycarbonates, which are not commercially available, can be synthesized by someone skilled in the art following and/or adapting the synthetic pathways known in the art as described e.g. for amino-modified polyethylene oxides. An example is adaptation of the following literature article included here by reference: McManus, N. T. et al., Journal of Applied Polymer Science (2006), 101(6), 4230-4237.

Test of Mechanical Properties:

The material according to example C1 is compared to PEBAX®

D) Formation of a Medical Balloon

Example D1

From the Material according to example C1 a length of a polymer tubing is formed by extrusion. The proximal and distal portions of the length of tubing is stretched to a reduced diameter while retaining an unstretched central portion, The lengths of polymer tubing is then radially expanded under pressure by expanding the tubing in a mold so that the balloon body is formed from the unstretched central portion of the tubing. The proximal and distal waist portions of the balloon are formed from the stretched proximal and distal portions of the tubing.

Example D2

From the Material according to example C1 a tubular segment with a predetermined wall thickness and length is formed by extrusion with a proximal end, a distal end and a center portion. The segment is then drawn to a predetermined length while maintaining the temperature of the segment below the highest glass transition temperature of the Co-Polymer according to examples C1 or C2. Thereby the proximal end forms a first waist. Following that, this segment with the first waist is expanded in a mold to produce the balloon. After finishing, the balloon has a body portion, wherein the center portion of the segment forms the balloon body portion.

The invention claimed is:

1. An implant or medical device comprising a co-polymer producible by polymerizing a modified polyamide with a polycarbonate diamine, characterized in that the modified polyamide is producible by contacting/mixing one or more un-modified polyamides with an α,ω-di-carboxylic acid, an alkyl ester of the α,ω-di-carboxylic acid, or an acyl halide of the α,ω-di-carboxylic acid and raising the temperature to above 150° C.

2. The implant or medical device according to claim 1 in which the implant or medical device is selected from the group consisting of a balloon, stent, stent graft, graft, graft connector and catheter.

3. The implant or medical device according to claim 1, wherein the polymerization is done by contacting the modified polyamide with the polycarbonate diamine, and raising the temperature to
  a. either above 150° C. in case of a melt polymerization or
  b. above 50° C. in case of a polymerization in solution.

4. The implant or medical device according to claim 1, wherein the α,ω-di-carboxylic acid is selected from the group consisting of oxalic acid malonic acid succinic acid fumaric acid glutaric acid adipic acid, 1,7-heptane-dicarboxylic acid, 1,8-octane-di-carboxylic acid, 1,9-nonane-di-carboxylic acid, 1,10-decane-di-carboxylic acid, 1,11-undecane-di-carboxylic acid, and 1,12-dodecane-di-carboxylic acid.

5. The implant or medical device according to claim 1, wherein the α,ω-di-carboxylic acid, the alkyl ester of the α,ω-di-carboxylic acid, or the acyl halide of the α,ω-di-carboxylic acid is a compound of general formula I

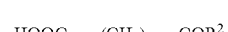
(I)

wherein
m is selected from a natural number between 1 and 10;
$R^2$ is selected from the group consisting of OH, halogen, and $OC_{1-4}$-alkyl.

6. The implant or medical device according to claim 5, wherein
m is 2, 3, 4 5, 6, 7, 8 or 9.

7. The implant or medical device according to claim 1, wherein the unmodified polyamides have a structure of general formula III or IIIa

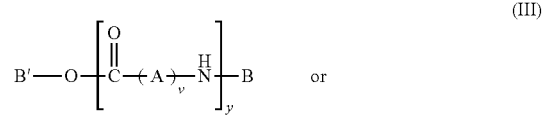
(III)

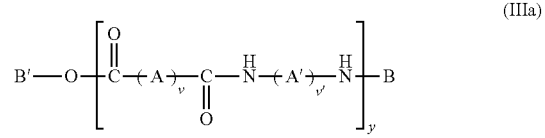
(IIIa)

wherein
A is a divalent, branched or linear, saturated or non-saturated hydrocarbon chain,
  wherein one or more hydrogen radicals of the hydrocarbon chain are optionally replaced with one of F, Cl, Br, I, $NH_2$, SH, or OH and
  wherein one or more carbon atoms of the hydrocarbon chain are optionally replaced by one of NH, O or S;

A' is a divalent, branched or linear, saturated or non-saturated hydrocarbon chain,
wherein one or more hydrogen radicals of the hydrocarbon chain are optionally replaced with one of F, Cl, Br, I, $NH_2$, SH, or OH, and
wherein one or more carbon atoms of the hydrocarbon chain are optionally replaced by one of NH, O or S;
B and B' independently from one another are selected from H or $C_{1-4}$-alkyl;
v is a natural number between 1 and 24;
v' is a natural number between 1 and 24;
y is a natural number >1 for Formula III and y is a natural number ≧1 for Formula IIIa.

8. The implant or medical device according to claim 7, wherein
A is a branched or linear, saturated or non-saturated, optionally substituted divalent aliphatic group;
A' is a branched or linear, saturated or non-saturated, optionally substituted divalent aliphatic group;
and/or
v is a natural number between 3 and 13;
v' is a natural number between 3 and 13.

9. The implant or medical device according to claim 1 wherein the one or more un-modified polyamides are selected from the group consisting of Nylon 6; Nylon 6,6; Nylon 11; and Nylon 12;
and
the α,ω-di-carboxylic acid is adipic acid.

10. The implant or medical device according to claim 1, wherein the α,ω-di-carboxylic acid, the alkyl ester of the α,ω-di-carboxylic acid, or the acyl halide of the α,ω-di-carboxylic acid is added in an amount resulting in a molar ratio between the α,ω-di-carboxylic acid and the one or more un-modified polyamides between 1.0 and 0.0005.

11. The implant or medical device according to claim 1, characterized in that the modified polyamide is of general formula IV or IVa v is a natural number between 1 and 24;
v' is a natural number between 1 and 24;
y is a natural number ≧1;
y' is a natural number ≧1 or 0; and
m is a natural number between 1 and 10.

12. The implant or medical device according to claim 11, characterized in that the modified polyamide is of general formula V

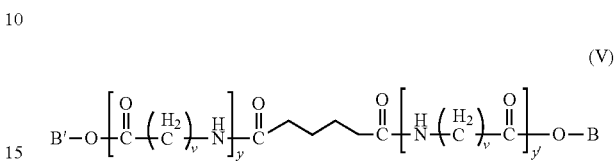

wherein,
B and B' independently from one another are selected from H or $C_{1-4}$-Alkyl;
v is a natural number between 1 and 24;
y is a natural number ≧1; and
y' is a natural number ≧1 or 0.

13. The implant or medical device according to claim 12, wherein the modified polyamide is a compound according to formula V, wherein
B and B' are hydrogen;
and/or
v is a natural number between 3 and 13;
and/or
y' is 0;
and/or
y+y' is between 20 and 2000.

14. The implant or medical device according to claim 1, wherein the polycarbonate diamine is of general formula VII or VIIa

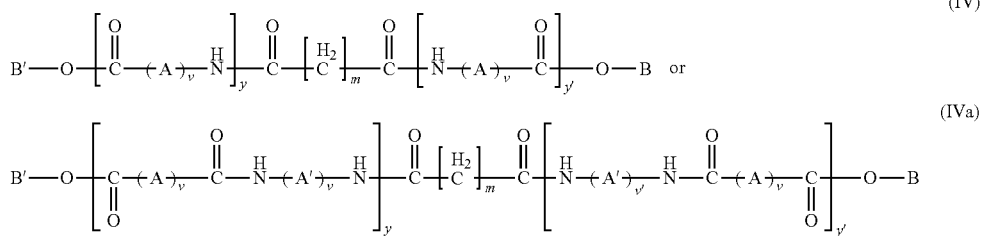

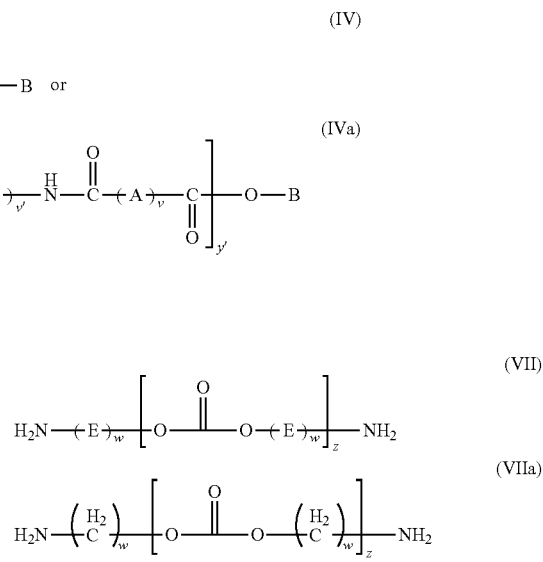

wherein
A is a divalent, branched or linear, saturated or non-saturated hydrocarbon chain,
wherein one or more hydrogen radicals of the hydrocarbon chain are optionally replaced with one of F, Cl, Br, I, $NH_2$, SH, OH and
wherein one or more carbon atoms of the hydrocarbon chain are optionally replaced by one of NH, O or S;
A' is a divalent, branched or linear, saturated or non-saturated hydrocarbon chain,
wherein one or more hydrogen radicals of the hydrocarbon chain are optionally replaced with one of F, Cl, Br, I, $NH_2$, SH, OH and
wherein one or more carbon atoms of the hydrocarbon chain are optionally replaced by one of NH, O or S;
B and B' independently from one another are selected from H or $C_{1-4}$-Alkyl;

wherein,
E is a divalent, branched or linear, saturated or non-saturated hydrocarbon chain,
wherein one or more hydrogen radicals of the hydrocarbon chain are optionally replaced with one of F, Cl, Br, I, $NH_2$, SH, OH and w is a natural number between 1 and 24; and z is a natural number $\geq 1$.

15. The implant or medical device according to claim 14, wherein the polycarbonate diamine is of general formula VIIa, wherein w is a natural number between 1 and 10; and/or z is a natural number between 1 and 2000.

16. The implant or medical device according to claim 1, wherein a reaction leading to the modified polyamide wherein the modified polyamide is produced by contacting/mixing one or more un-modified polyamides with one of a mono-substituted α,ω-di-carboxylic acid, an alkyl ester of the α,ω-di-carboxylic acid, or an acyl halide of the α,ω-di-carboxylic acid and raising the temperature to above 150° C; or a polymerization reaction for producing a Co-Polymer produced by polymerizing a modified polyamide with a polycarbonate diamine; or both reactions is/are executed using reactive extrusion.

17. An implant or medical device according to formula XI, XIa, XIb or XIc,

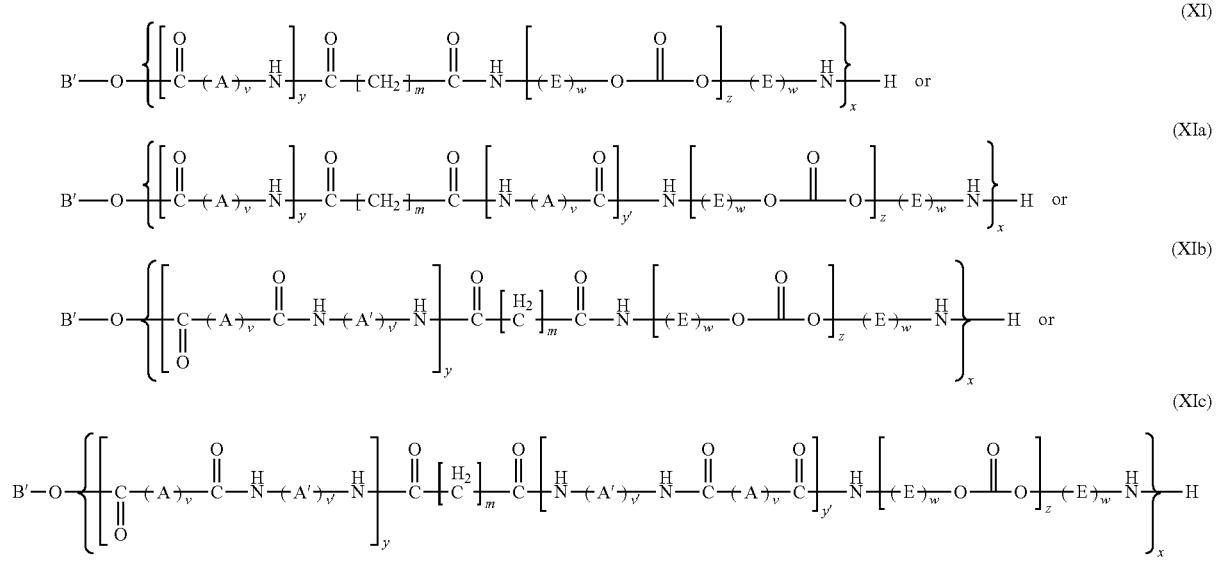

wherein,

A is a divalent, branched or linear, saturated or non-saturated hydrocarbon chain,
  wherein one or more hydrogen radials of the hydrocarbon chain are optionally replaced with one of F, Cl, Br, I, $NH_2$, SH, OH and
  wherein one or more carbon atoms of the hydrocarbon chain are optionally replaced by one of NH, O or S;

A' is a divalent, branched or linear, saturated or non-saturated hydrocarbon chain,
  wherein one or more hydrogen radials of the hydrocarbon chain are optionally replaced with one of F, Cl, Br, I, $NH_2$, SH, OH and
  wherein one or more carbon atoms of the hydrocarbon chain are optionally replaced by one of NH, O or S;

E is a divalent, branched or linear, saturated or non-saturated hydrocarbon chain,
  wherein one or more hydrogen radials of the hydrocarbon chain are optionally replaced with one of F, Cl, Br, I, $NH_2$, SH, OH;

B' is selected from H or $C_{1-4}$-alkyl;

v is a natural number between 1 and 24;

v' is a natural number between 1 and 24;

w is a natural number between 1 and 24;

x is a natural number $\geq 1$;

y and y' independently from one another are a natural number $\geq 1$;

z is a natural number $\geq 1$; and m is a natural number between 1 and 10.

18. The implant or medical device according to claim 17 of general formula XIII or XIIIa

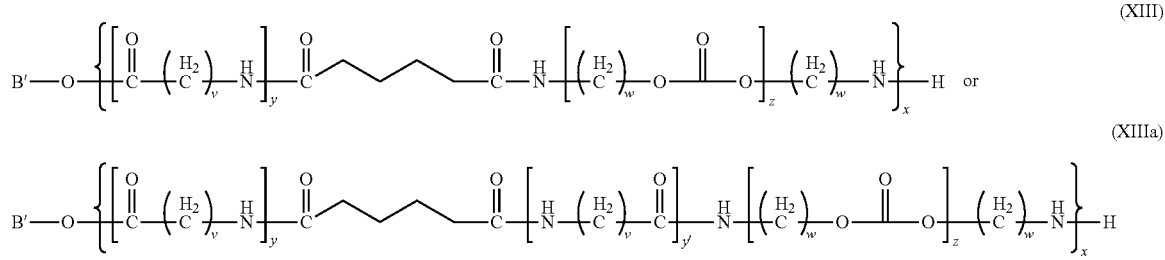

wherein,
B' is selected from H or $C_{1-4}$-Alkyl;
v is a natural number between 1 and 24;
w is a natural number between 1 and 24;
x is a natural number $\geq 1$;
y and y' independently from one another are a natural number $\geq 1$; and
z is a natural number $\geq 1$.

19. The implant or medical device according to claim 17, wherein
B' is hydrogen;
and/or
A is —CH—;
and/or
E is —CH—;
and/or
v is a natural number between 3 and 13;
and/or
w is a natural number between 1 and 10;
and/or
z is a natural number between 1 and 2000;
and/or
y is a natural number between 1 and 2000; and
y' is a natural number between 1 and 2000; and
the sum of y+y' is a natural number between 1 and 2000;
and/or
x is a natural number between 1 and 100.

20. The implant or medical device according to claim 19, wherein
v is 11; and
w is 6.

21. The implant or medical device according to claim 17, wherein the co-polymer is modified in at least one of the end groups B with liquid crystalline oligomers.

22. An implant or medical device comprising a co-polymer, wherein the co-polymer includes units derived from polyamide-forming monomers, units derived from polycarbonate diamines and units derived from an α,ω-di-carboxylic acid,
wherein the polyamide-forming monomers are represented by the following formulas (IX) or (IXa), the polycarbonate diamines are represented by the following formula (VII) or (VIIa) and the α,ω-di-carboxylic acids are represented by the following formula (I):

(IX)

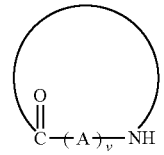

(IXa)

wherein,
A is a divalent, branched or linear, saturated or non-saturated hydrocarbon chain,
wherein one or more hydrogen radicals of the hydrocarbon chain are optionally replaced with one of F, Cl, Br, I, $NH_2$, SH, OH and
wherein one or more carbon atoms of the hydrocarbon chain are optionally replaced by one of NH, O or S;
and
v is a natural number between 1 and 24;

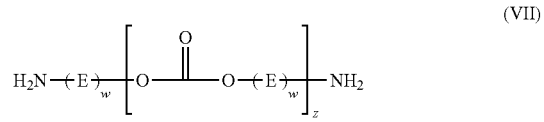

(VII)

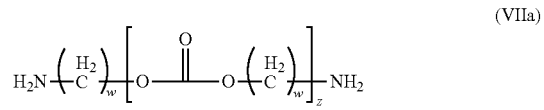

(VIIa)

wherein,
E is a divalent, branched or linear, saturated or non-saturated hydrocarbon chain,
wherein one or more hydrogen radicals of the hydrocarbon chain are optionally replaced with one of F, Cl, Br, I, $NH_2$, SH, OH;
w is a natural number between 1 and 24;
z is a natural number $\geq 1$;

(I)

wherein,
m is selected from a natural number between 1 and 10;
$R_2$ is selected from the group of OH, halogen and $OC_{1-4}$-alkyl.

23. The implant or medical device according to claim 22, wherein

A is —$CH_2$—;

and/or v is a natural number between 3 and 13;

and/or

E is —$CH_2$—;

and/or w is a natural number between 1 and 10;

and/or z is a natural number between 1 and 2000;

and/or m is selected from a natural number between 1 and 10;

and/or $R_2$ is selected from the group consisting of OH, halogen and $OC_{1-4}$-alkyl.

24. A medical balloon for a medical device formed from a length of polymer tubing by radial expansion of the tubing under pressure, the polymer being a co-polymer produced by polymerizing a modified polyamide with a polycarbonate diamine, characterized in that the modified polyamide is produced by contacting/mixing one or more unmodified polyamides with an α,ω-di-carboxylic acid, an akyl ester of the α,ω-di-caboxylic acid, or an acyl halide of the α,ω-di-carboxylic acid and raising the temperature to above 150 ° C.

* * * * *

UNITED STATES PATENT AND TRADEMARK OFFICE
CERTIFICATE OF CORRECTION

PATENT NO. : 8,492,484 B2
APPLICATION NO. : 12/599275
DATED : July 23, 2013
INVENTOR(S) : Günter Lorenz It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 718 days.

Signed and Sealed this
Eighth Day of September, 2015

Michelle K. Lee
*Director of the United States Patent and Trademark Office*